United States Patent
Jaworowicz

(12) 
(10) Patent No.: US 6,451,347 B1
(45) Date of Patent: Sep. 17, 2002

(54) METHOD FOR PURIFYING HUMAN GROWTH HORMONE

(75) Inventor: Warren E. Jaworowicz, Boxboro, MA (US)

(73) Assignees: Alkermes Controlled Therapeutics, Inc., Cambridge, MA (US); Genentech, Inc., San Francisco, CA (US)

( * ) Notice: Subject to any disclaimer, the term of this patent is extended or adjusted under 35 U.S.C. 154(b) by 0 days.

(21) Appl. No.: 09/260,362

(22) Filed: Mar. 1, 1999

(51) Int. Cl.$^7$ .................. A61K 38/27; A61K 47/30; C07K 1/32; C07K 14/61
(52) U.S. Cl. ................... 424/486; 514/21; 530/399
(58) Field of Search ................... 530/399, 419, 530/420; 424/486, 422, 423, 424, 425, 426, 484, 485, 487, 488; 514/12, 21

(56) References Cited

U.S. PATENT DOCUMENTS

| | | | |
|---|---|---|---|
| 4,898,830 A | 2/1990 | Goeddel et al. | 435/320 |
| 4,985,404 A * | 1/1991 | Mitchell | 514/6 |
| 5,654,010 A | 8/1997 | Johnson et al. | 424/502 |
| 5,667,808 A * | 9/1997 | Johnson | 424/501 |
| 5,763,394 A | 6/1998 | O'Connor et al. | 514/12 |
| 5,891,478 A | 4/1999 | Johnson et al. | 424/502 |
| 6,087,324 A * | 7/2000 | Igari | 514/2 |

FOREIGN PATENT DOCUMENTS

| | | | |
|---|---|---|---|
| EP | 0 216 485 | * | 4/1987 |
| WO | WO 92/00998 | | 1/1992 |
| WO | WO 94/12158 | | 9/1994 |
| WO | WO 95/29664 | | 11/1995 |
| WO | WO 96/40074 | | 12/1996 |

OTHER PUBLICATIONS

Yu–Chang John Wang, et al., "Parenteral Formulations of Proteins and Peptides: Stability and Stabilizers," *Journal of Parenteral Science and Technology*, 42(2S): S3–S26 (1988).

Cunningham, B.C., et al., "Dimerization of Human Growth Hormone by Zinc," *Science*, 253: 545–548 (Aug. 2, 1991).

* cited by examiner

*Primary Examiner*—Jeffrey E. Russel
(74) *Attorney, Agent, or Firm*—Hamilon, Brook, Smith & Reynolds, P.C.

(57) ABSTRACT

A method of purifying human growth hormone (hGH) from deamidated hGH, oxidized hGH or both. The method comprises the steps of forming a metal cation complexed-hGH composition enriched in native hGH under conditions wherein none or less than all of the deamidated hGH, oxidized hGH or both complex with a metal cation and, isolating the metal cation-complexed hGH composition from the deamidated hGH, oxidized hGH or combination thereof. The method can further comprise the step of releasing purified hGH from the complex. Alternatively, the metal cation-complexed hGH can be encapsulated into a biocompatible polymer for sustained release of hGH. The purification method can be performed one or more times using the hGH released from the metal cation-complexed hGH composition, depending on the purity of the hGH desired.

10 Claims, 2 Drawing Sheets

METHOD FOR PURIFYING HUMAN GROWTH HORMONE

BACKGROUND OF THE INVENTION

Human growth hormone (hGH) is a protein secreted by the pituitary gland which consists of 191 amino acids and has a molecular weight of about 21,500. hGH can also be produced by recombinant genetic engineering. Two species of note which are obtained recombinantly are the 191 amino acid native species (somatropin), and the 192 amino acid N-terminal methionine (met) species (somatrem). hGH will cause growth in all bodily tissues which are capable of growth.

hGH is typically used to treat patients suffering from hypopituitary dwarfism. hGH can be administered, for example, as a subcutaneous bolus three times a week, or once daily, to patients to maintain suitable serum levels of hGH. For patients chronically receiving hGH, this method of frequent injections often results in poor patient compliance. An alternative to the use of repetitive injections, can be found in the use of sustained release devices comprising a polymeric matrix of a biocompatible polymer and particles of biologically active, metal cation-stabilized hGH dispersed within in the polymer, as described in U.S. Pat. No. 5,667,808 to Johnson et al. the entire content of which is hereby incorporated by reference.

SUMMARY OF THE INVENTION

It has been found that the formation of a metal cation complexed hGH is inhibited by the presence of degradation products, in particular, deamidated and oxidized forms of hGH. Consequently, the complexation of native hGH is more complete than the complexation of the deamidated and oxidized forms resulting from degradation of the protein. In view of the above, this invention relates to a method of purifying human growth hormone (hGH) from deamidated hGH, oxidized hGH or both. The method comprises the steps of forming a metal cation-complexed hGH composition enriched in native hGH under conditions wherein none or less than all of the deamidated hGH, oxidized hGH or both complex with a metal cation and, isolating the metal cation-complexed hGH composition from the deamidated hGH, oxidized hGH or a combination thereof. The method can further comprise releasing hGH from the complex. Alternatively, the metal cation-complexed hGH can be encapsulated into a biocompatible polymer for sustained release of hGH. The method can be performed one or more times with the hGH released from the metal cation-complexed hGH composition. The method can be repeated until the desired level of purity for the hGH is reached.

In a specific embodiment, native human growth hormone is purified from deamidated hGH, oxidized hGH or both by making an aqueous solution of an hGH composition comprising native hGH, and one or both deamidated hGH and oxidized hGH and adding a metal cation component to said aqueous solution under conditions wherein none or less than all of the deamidated hGH, oxidized hGH or both complex with the metal cation component thereby forming a metal cation-complexed hGH composition enriched in native hGH as compared to said aqueous composition of hGH. The metal cation-complexed hGH composition is then precipitated and the precipitate can be isolated. The method can further comprise the step of releasing the hGH from the metal cation-complexed hGH composition. The method can be repeated one or more times with the hGH released from the metal cation-complexed hGH composition, depending on the level of purity desired.

In another embodiment, the metal cation-complexed hGH composition prepared according to the method of the invention can be encapsulated into a biocompatible polymer for sustained release of human growth hormone, for example, as described in U.S. Pat. No. 5,667,808 to Johnson et al. the entire content of which is hereby incorporated by reference.

The method of the invention provides a simple and cost efficient method of purifying hGH, in particular, for removing deamidated and oxidized impurities.

DETAILED DESCRIPTION OF THE INVENTION

Figure 1:
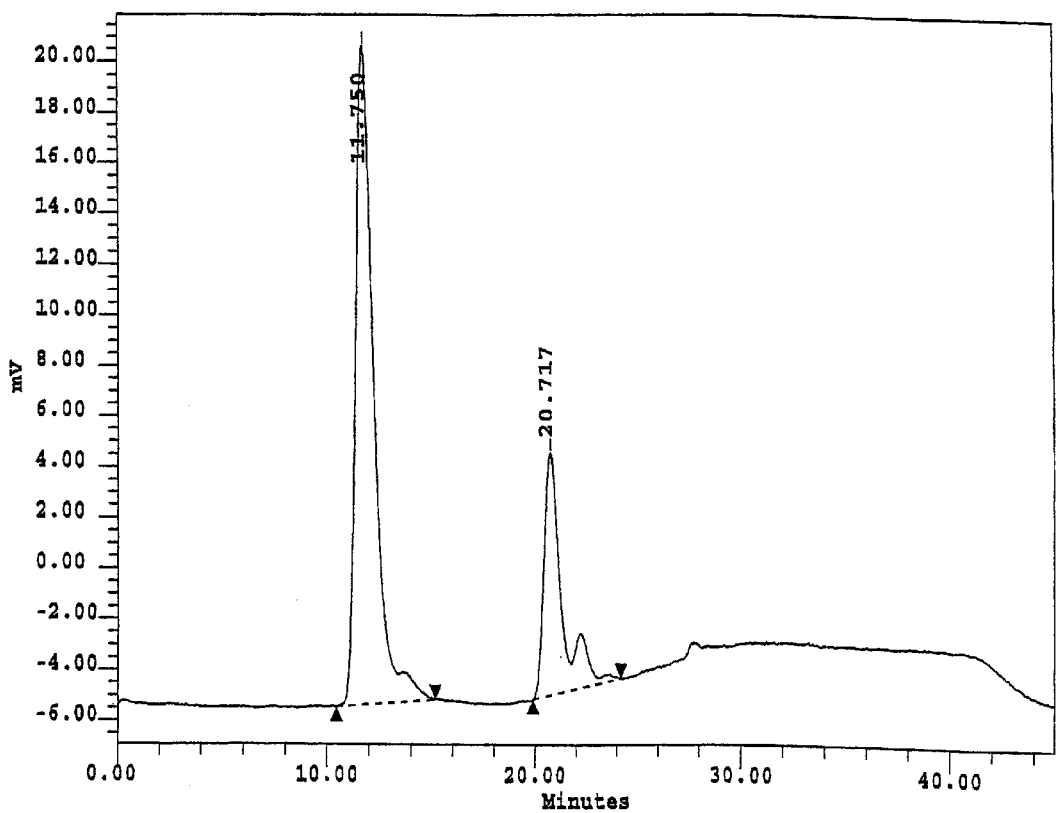
FIG. 1 is a chromatogram resulting from Ion Exchange Chromatographic Analysis of a solution of unpurified hGH at a concentration of 20 mg/mL.
Figure 2:
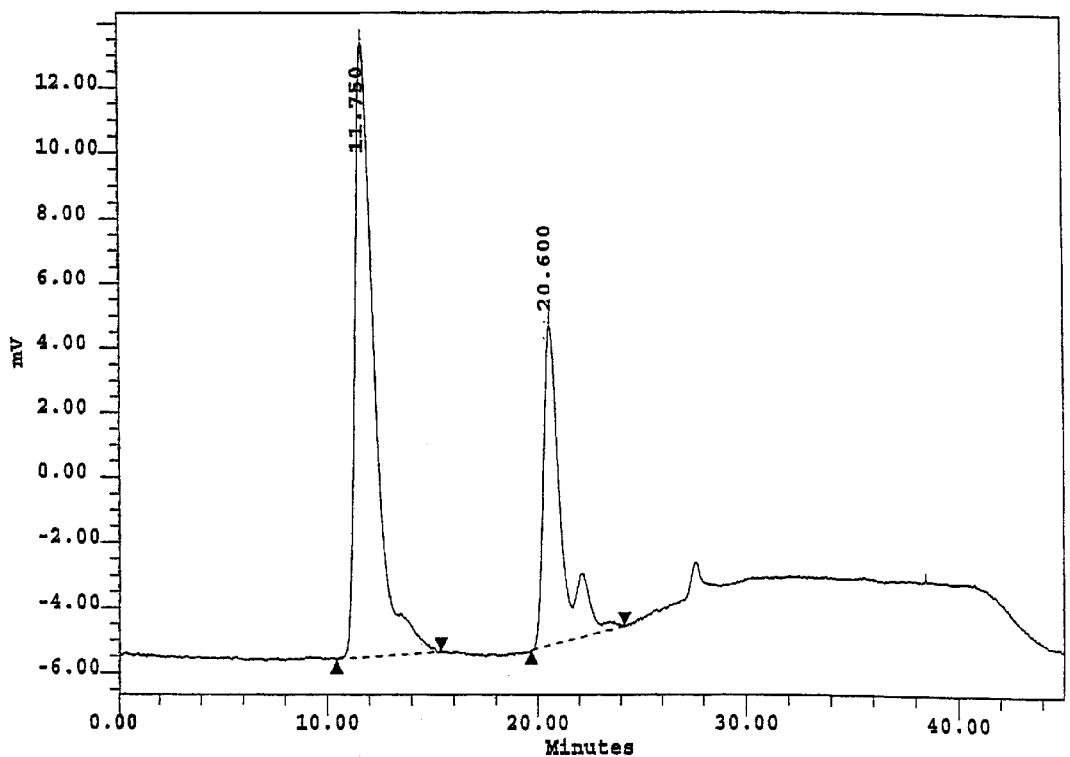
FIG. 2 is a chromatogram resulting from Ion Exchange Chromatographic analysis of the supernatant resulting from complexation of hGH to zinc at a molar ratio of 6:1 zinc cation component to hGH and a final concentration of 5mg/mL.

"Human growth hormone" or "hGH" as that term is used herein denotes human growth hormone produced by methods including natural source extraction and purification, and by recombinant cell culture systems. Its sequence and characteristics are set forth, for example, in *Hormone Drugs*, Gueriguian et al., U.S.P. Convention, Rockville, Md. (1982). The terms likewise cover biologically active human growth hormone equivalents, for example, differing in one or more amino acid(s) in the overall sequence. Furthermore, the terms as used herein are intended to cover substitution, deletion and insertion amino acid variants of hGH, or posttranslational modifications. Two species of note are the 191 amino acid native species (somatropin) and the 192 amino acid N-terminal methionine (met) species (somatrem) commonly obtained recombinantly.

hGH undergoes several degradative pathways including, for example, deamidation, oxidation of methionine residues, aggregation, and clipping of the peptide backbone. The purification method described herein is directed to removal of the degradation products, in particular, those resulting from deamidation and oxidation.

"Deamidation" as that term is used herein, is the hydrolysis of the side chain amide found on the amino acids glutamine and asparagine, when present in a polypeptide or protein. Deamidation is a major route of degradation for many proteins, such as hGH. Deamidation occurs almost exclusively through an imide pathway. Although solvent hydrolysis can also cause deamidation of the side chain amide of glutamine and asparagine, when present in a polypeptide or protein, this pathway is less common. The most common sites for deamidation are the asparagine residues found at positions 149 and 152 of the hGH amino acid sequence (See e.g., Perlman, Stability and Characterization of Protein; Peptide Drugs, Chapter 1, p 28, Plenum Press, 1993).

"Oxidation" as that term is used herein refers to oxidation of methionine, cysteine and/or tryptophan residues present in the hGH sequence. Oxidation is promoted at both neutral and basic pH. Disulfide bridging of methionine residues is the main site of oxidation in the hGH sequence (See e.g., Perlman, Stability and Characterization of Protein; Peptide Drugs, Chapter 1, p 28, Plenum Press, 1993).

This invention relates to a method of purifying human growth hormone (hGH) from deamidated hGH, oxidized hGH or both. The method comprises the steps of forming a metal cation-complexed hGH composition enriched in native hGH under conditions wherein none or less than all of the deamidated hGH, oxidized hGH or both complex with a metal cation and, isolating the metal cation-complexed hGH composition from the deamidated hGH, oxidized hGH or a combination thereof. The method can further comprise the step of releasing hGH from the complex. Alternatively, the metal cation-complexed hGH can be encapsulated into a biocompatible polymer for sustained release of hGH. The method can be performed one or more times with the hGH released from the metal cation-complexed hGH composition. The number of times the method is repeated can be determined based on the level of purity desired for the hGH.

In a specific embodiment, native human growth hormone is purified from deamidated hGH, oxidized hGH or both by making an aqueous solution of an hGH composition comprising native hGH, and one or both deamidated hGH and oxidized hGH and adding a metal cation component to said aqueous solution under conditions wherein none or less than all of the deamidated hGH, oxidized hGH or both complex with the metal cation component thereby forming a metal cation-complexed hGH composition enriched in native hGH as compared to said aqueous composition of hGH. The metal cation-complexed hGH composition is then precipitated and the precipitate can be isolated. The method can further comprise the step of releasing the hGH from the metal cation-complexed hGH composition. The method can be repeated one or more time with the hGH released from the metal cation-complexed hGH composition, depending on the level of purity desired.

In another embodiment, the metal cation-complexed hGH composition prepared according to the method of the invention can be encapsulated into a biocompatible polymer for sustained release of human growth hormone, for example, as described in U.S. Pat. No. 5,667,808 to Johnson et al. the entire content of which is hereby incorporated by reference.

Suitable metal cations include metal cations contained in biocompatible metal cation components. A metal cation component is biocompatible if the cation component is non-toxic to the recipient, in the quantities used, and also presents no significant deleterious or untoward effects on the recipient's body, such as an immunological reaction at the injection site. In addition, the metal cation should not significantly oxidize the hGH under the conditions used. In a preferred embodiment, the metal cation is multivalent, for example, having a valency of $^+2$ or more. Examples of suitable metal cations include, but are not limited to $K^+$, $Zn^{+2}$, $Mg^{+2}$ and $Ca^{+2}$. Suitable metal cation also include cations of transition metals, such as $Cu^{+2}$.

Typically, the molar ratio of metal cation component to hGH, for the metal cation complexing to the hGH, is about 10:1 or less. For example, from about 1:1 to about 10:1, such as, 8:1, 6:1, 4:1 and 2:1. However, the ratio of metal cation component to hGH which gives the desired level of complexation of native hGH can be determined by one of skill in the art employing the teachings described herein.

A preferred metal cation used to complex hGH is $Zn^{+2}$. In a more preferred embodiment, the molar ratio of metal cation component, containing $Zn^{+2}$ cations, to hGH is about 6:1.

The suitability of a metal cation for complexation of hGH can be determined by one of ordinary skill in the art by performing a variety of techniques such as polyacrylamide gel electrophoresis, isoelectric focusing, reverse phase chromatography, HPLC and potency tests on hGH subsequent to release from the metal cation-hGH complex.

To prepare a metal cation complexed-hGH composition, hGH is mixed in a suitable aqueous solvent with at least one suitable metal cation component under pH conditions suitable for forming a complex of metal cation and hGH. Typically, the complexed hGH will be in the form of a cloudy precipitate, which is suspended in the solvent. In a preferred embodiment, hGH is complexed with $Zn^{+2}$. In an even more preferred embodiment, the $Zn^{+2}$-hGH complex is prepared using zinc acetate as the metal cation component.

Suitable pH conditions to form a complex of hGH typically include pH values between about 6.0 and about 9.0. Suitable pH conditions are typically achieved through use of an aqueous buffer, such as sodium bicarbonate, as the solvent.

Suitable solvents are those in which the hGH and the metal cation component are each at least slightly soluble, such as in an aqueous sodium bicarbonate buffer. For aqueous solvents, it is preferred that water used be either deionized water or water-for-injection (WFI).

It is understood that the hGH can be in a solid or a dissolved state, prior to being contacted with the metal cation component. It is also understood that the metal cation component can be in a solid or a dissolved state, prior to being contacted with the hGH. In a preferred embodiment, a buffered aqueous solution of hGH is mixed with an aqueous solution of the metal cation component. It is to be understood that both the hGH and metal cation component cannot be in solid form when forming the complex.

Typically, the complexed hGH will be in the form of a cloudy precipitate, which is suspended in the solvent. In an even more preferred embodiment, hGH is complexed with $Zn^{+2}$. The complexed hGH can then be isolated from the non-complexed hGH using conventional isolation techniques. For example, when the complex is present as a solid any means of solid/liquid separation, for example, centrifugation or filtration can be employed.

Optionally, the purified hGH can be released from the metal cation complexed-hGH composition, by adding an anionic component having an anion, which competes with hGH to form an insoluble complex with the metal cation which is complexed to the hGH. For example, the anionic component can be sodium phosphate, wherein the phosphate anion competes with the hGH to form an insoluble complex containing the metal cation which is complexed to hGH. For example, $ZnPO_4$ can be formed as the insoluble complex when the metal cation of the hGH complex is zinc. The anionic component can be added either as a solid or in solution to an aqueous suspension of the metal cation complexed hGH, resulting in formation of an insoluble complex of the metal cation of the hGH and the anion of the anionic component. The purified hGH can then be separated from the insoluble complex and dried, such as by lyophilization, to yield a purified form of hGH. Acceptable means to lyophilize the purified hGH include those known in the art.

Alternatively, the metal cation-complexed hGH can be encapsulated into a biocompatible polymer matrix for sustained release using any known methods of encapsulation. In a preferred embodiment, encapsulation is accomplished following the method described in U.S. Pat. No. 5,667,808 to Johnson et al., the entire contents of which is incorporated herein by reference. Methods for forming a sustained release composition are further described in U.S. Pat. No. 5,019,400 issued to Gombotz et al., and U.S. patent application Ser. No. 08/443,726, filed May 18, 1995, now U.S. Pat. No. 5,992,253 the entire teachings of which are incorporated herein by reference. These methods of microparticle formation, as compared with other methods such as phase separation, can reduce the amount of active agent required to produce a sustained release composition.

In the referenced methods, a solution of a biocompatible polymer, also containing the metal cation-complexed hGH or other active agent which can be present in solution or as a particle dispersion, is processed to create droplets, wherein at least a significant portion of the droplets contain polymer, polymer solvent and the active agent, for example, metal cation-complexed hGH. These droplets are then frozen by means suitable to form microparticles. Means suitable to form droplets include directing the solution through an ultrasonic nozzle, pressure nozzle, Rayleigh jet, or by other known means for creating droplets from a solution.

Means suitable for freezing droplets to form microparticles include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, a combination of ethanol and hexane, pentane or oil.

The solvent in the frozen microdroplets is extracted as a solid and/or liquid into the non-solvent to form active agent, for example, hGH containing microparticles.

Polymers suitable to form a polymer matrix of the sustained release composition of this invention are biocompatible polymers which can be either biodegradable or non-biodegradable polymers or blends or copolymers thereof. A polymer is biocompatible if the polymer and any degradation products of the polymer are non-toxic to the recipient and also possess no significant deleterious or untoward effects on the recipient's body, such as an immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly (lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is between about 2,000 Daltons to about 2,000,000 Daltons. In a preferred embodiment, the polymer is biodegradable polymer or copolymer. In a more preferred embodiment, the polymer is a poly(lactide-co-glycolide)(hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons.

The invention will now be further and specifically described by the following examples.

Exemplifications

Nondenaturing Ion Exchange Chromatography (IEC) was conducted on a 7.5 mm×7.5 cm TSK-GEL column (DEAE-SPW 10 $\mu$M) available from the Nest Group (Cat. #: 07164) using a precolumn filter (Upchurch Scientific, Cat. #: A314) having a $2\mu$ frit (Upchurch Scientific, Cat. #: C-V3X). The flow rate was 0.5 ml/min with a column load of between 0.5 and 2.0 $\mu$g and detector settings at an excitation wavelength of 286 nm and an emission wavelength of 336 nm. The elution system consisted of Mobile Phase A (HPLC grade water) and Mobile Phase B (0.125 M $KH_2PO_4$, 10% (v/v) Acetonitrile at about pH 5.8) employing the following gradient:

| Time | % A | % B | Curve type |
| --- | --- | --- | --- |
| 0.0 | 60 | 40 | isocratic |
| 3.0 | 60 | 40 | linear |
| 13.0 | 0 | 100 | isocratic |
| 27.0 | 0 | 100 | linear |
| 28.0 | 60 | 40 | isocratic |
| 45.0 | 60 | 40 | isocratic |

Size Exclusion Chromatography (SEC) was used to determine the native monomeric hGH in an aqueous solution. SEC was conducted on a 7.8 mm×30 cm G2000SWXL column available from the Nest Group (Cat. #: 08540) using a precolumn filter (Upchurch Scientific, Cat. #: A314) having a 2 $\mu$ frit (Upchurch Scientific, Cat. #: C-V3X). The flow rate was 1.0 mL/min with a column load of between 2.5 and 15.0 $\mu$g and a detector setting of 214 nm. The mobile phase consisted of 0.05 M $NaH_2PO4$, 0.15 M NaCl, pH 7.2±0.1.

Reversed Phase HPLC (rHPLC) was conducted on a 150 mm×4.6 mm PLRP-S column (I.D. $8\mu$, 300 Å) available from Upchurch Scientific (Part #: 1512-3801) using a precolumn filter (Upchurch Scientific, Cat. #: A314) having a $2\mu$ frit (Upchurch Scientific, Cat. #: C-V3X). The flow rate was 2.0 mL/min with a run time of 22 minutes. A column load of between 2.0 and 10 $\mu$g and detector settings at an excitation wavelength of 286 nm and an emission wavelength of 335 nm were employed. The elution system consisted of Mobile Phase A (440 mL of acetonitrile to 1.0 L of 50 mM phosphate Buffer) and Mobile Phase B (1.0 L of acetonitrile to 1.0 L of 50 mM phasphate buffer) employing the following gradient:

| Time | % A | % B | Curve type |
| --- | --- | --- | --- |
| 0.0 | 60 | 40 | linear |
| 15.0 | 0 | 100 | linear |
| 17.0 | 0 | 100 | isocratic |
| 17.5 | 60 | 40 | linear |
| 35.0 | 60 | 40 | linear |

EXAMPLE 1

Formation of $Zn^{+2}$-Complexed hGH

Human growth hormone (hGH), whose DNA sequence is described in U.S. Pat. No. 4,898,830, issued to Goeddel et al., was used in this example. The human growth hormone was initially in the form of a solution having a concentration of 25 mg/mL hGH in 23 mM sodium bicarbonate, at a pH of 8.4. A second solution of hGH having a concentration of 12.5 mg/ml, was also employed in this example by appropriate dilution of the initial solution with 4 mM NaHCO$_3$ (pH=7.2).

A 0.9 mM Zn$^{+2}$ solution was prepared from deionized water and zinc acetate dihydrate. The required amount of the zinc cation component was added to each hGH solution (25 mg/mL and 12.5 mg/mL concentrations) to form Zn$^{+2}$-hGH complexes using a 6:1, 8:1 and 10:1 molar ratio of Zn$^{+2}$ cation component to hGH, as shown in Table 1. A cloudy suspended precipitate comprising Zn$^{+2}$-stabilized hGH was formed at both concentrations of hGH and for each molar ratio. The final concentration of hGH in the diluted sample (12.5 mg/mL) was 5 mg/mL, and in the undiluted samples was 20 mg/mL.

TABLE 1

COMPLEXATION OF hGH

| Complexed at 5 mg/mL from bulk at 12.5 mg/mL | | | | | Complexed at 20 mg/mL from bulk at 25 mg/mL | | | | |
| --- | --- | --- | --- | --- | --- | --- | --- | --- | --- |
| Sample # | Complexation Ratio | Bulk Drug (mL) | Zn (OAc)$_2$ (mL) | Zn (OAc)$_2$ (mM) | Sample # | Complexation Ratio | Bulk Drug (mL) | Zn (OAc)$_2$ (mL) | Zn (OAc)$_2$ (mM) |
| 1 | 10:1 | 5 | 7.5 | 3.8 | 4 | 10:1 | 5 | 1.25 | 45.5 |
| 2 | 8:1 | 5 | 7.5 | 3.0 | 5 | 8:1 | 5 | 1.25 | 36.4 |
| 3 | 6:1 | 5 | 7.5 | 2.3 | 6 | 6:1 | 5 | 1.25 | 27.3 |

The precipitate was pelleted by centrifugation at about 13,200 rpm for approximately one minute. A sample of the supernatant was assayed by IEC, SEC and rHPLC to determine the ratio of native hGH to the deamidated and oxidized degradation products. The ratio of native hGH and the deamidated and oxidized degradation products was compared to hGH prior to purification. The results are shown in Table 2.

The results demonstrate that the percentage of deamidated and oxidized hGH present in the supernatant, when compared to a solution of hGH prior to purification was greater.

TABLE 2

ANALYSIS OF SUPERNATANT AND COMPARISON TO UNPURIFIED hGH STARTING MATERIAL

| Sample # | % Native hGH: Deamidated in Supernatant (As Determined by IEC) | % Native hGH: Oxidized hGH (As Determined by rHPLC) | % Monomeric hGH (As Determined by SEC) |
| --- | --- | --- | --- |
| Control-Unpurified hGH (Average of two runs) | 73.55:26.45 | 94.9:5.1 | 92.55 |
| 1 (10:1 complexed at 5 mg/mL) | 69:31 | — | 96 |
| 2 (8:1 complexed at 5 mg/mL) | 70:30 | — | 96 |
| 3 (6:1 complexed at 5 mg/mL) | 66.8:33.2 | 94.5:5.5 | 98.5 |
| 5 (8:1 complexed at 20 mg/mL) | 71:29 | — | 97 |
| 6 (6:1 complexed at 20 mg/mL | 64:36 | — | 97.2 |

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A method of purifying a human growth hormone composition comprising the steps of:
    a) providing an aqueous solution of a hGH composition wherein said hGH composition comprises a native hGH, and one or both deamidated hGH and oxidizes hGH;
    b) adding a metal cation component to said aqueous solution thereby forming a metal cation-complexed hGH composition enriched in native hGH as compared to said hGH composition;
    c) precipitating the enriched metal cation-complexed hGH composition; and
    d) isolating the precipitate.

2. A method of forming a composition for the sustained release of human growth hormone from a polymer matrix comprising the steps of:
    a) providing an aqueous solution of a hGH composition wherein said hGH composition comprises a native hGH, and one or both deamidated hGH and oxidized hGH;
    b) adding a metal cation component to said aqueous solution thereby forming a metal cation-complexed hGH composition enriched in native hGH as compared to said hGF composition;
    c) precipitating the enriched metal cation-complexed hGH composition;
    d) isolating the precipitate; and
    e) encapsulating the enriched metal cation complexed hGH composition in a biocompatible polymer.

3. The method of claim 1, further comprising the step of releasing hGH from the precipitate.

4. The method of claim 3, wherein the method is repeated one or more times with the hGH released from the precipitation.

5. The method of claim 1 wherein the metal cation of the metal cation-complexed hGH composition is selected from the group consisting of Zn$^{+2}$, Mg$^{+2}$, Ca$^{+2}$, and K+.

6. The method of claim 5, wherein a metal cation component to hGH molar ratio of about 10:1 or less is used to prepare the metal cation-complexed hGH composition.

7. The method of claim 6, wherein the metal cation is zinc.

8. The method of claim 7, wherein the molar ratio of metal cation component to hGH is about 6:1.

9. The method of claim 2, wherein the biocompatible polymeric matrix is selected from the group consisting of: poly(lactides), poly(glycolides), poly(lactide-co-glycolides), poly(lactic acids)s, poly(glycolic acids)s, poly(lactide acid-co-glycolic acids)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends and copolymers thereof.

10. The method of claim 9 wherein said polymer comprises poly(lactide-co-glycolide).

* * * * *

UNITED STATES PATENT AND TRADEMARK OFFICE
CERTIFICATE OF CORRECTION

PATENT NO.   : 6,451,347 B1
DATED        : September 17, 2002
INVENTOR(S)  : Warren E. Jaworowicz It is certified that error appears in the above-identified patent and that said Letters Patent is hereby corrected as shown below:

<u>Column 8,</u>
Line 34, insert -- biocompatible -- before the word "polymer".
Line 43, delete "hGF" and insert -- hGH --.
Line 47, delete "enriched metal-cation complexed hFGH compositions" and insert -- precipitate --.
Line 64, delete "polymeric matrix" and insert -- polymer --.

Signed and Sealed this

Twenty-eighth Day of January, 2003

JAMES E. ROGAN
*Director of the United States Patent and Trademark Office*